United States Patent
Pyayt et al.

(10) Patent No.: US 11,307,194 B2
(45) Date of Patent: Apr. 19, 2022

(54) SYSTEMS AND METHODS FOR ANALYZING LIQUIDS

(71) Applicant: UNIVERSITY OF SOUTH FLORIDA, Tampa, FL (US)

(72) Inventors: Anna Pyayt, Tampa, FL (US); Edikan Archibong, Riverview, FL (US); Harry Tuazon, North Charleston, SC (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 79 days.

(21) Appl. No.: 15/311,216

(22) PCT Filed: May 18, 2015

(86) PCT No.: PCT/US2015/031366
§ 371 (c)(1),
(2) Date: Nov. 15, 2016

(87) PCT Pub. No.: WO2015/179288
PCT Pub. Date: Nov. 26, 2015

(65) Prior Publication Data
US 2017/0082602 A1 Mar. 23, 2017

Related U.S. Application Data

(60) Provisional application No. 62/000,130, filed on May 19, 2014.

(51) Int. Cl.
*B01L 3/00* (2006.01)
*A61B 5/1455* (2006.01)
(Continued)

(52) U.S. Cl.
CPC .......... *G01N 33/49* (2013.01); *A61B 5/1455* (2013.01); *A61B 5/14552* (2013.01);
(Continued)

(58) Field of Classification Search
None
See application file for complete search history.

(56) References Cited

U.S. PATENT DOCUMENTS 4,892,383 A * 1/1990 Klainer .............. G01N 21/7703
250/226
4,925,268 A * 5/1990 Iyer .................... A61B 5/14539
385/12
(Continued)

FOREIGN PATENT DOCUMENTS

EP 2281186 A2 2/2011

OTHER PUBLICATIONS

Archibong, et al., "Optofluidic spectroscopy integrated on optical fiber platform", Sensing and Bio-Sensing Research 3, 2015.
(Continued)

*Primary Examiner* — Neil N Turk
(74) *Attorney, Agent, or Firm* — Quarles & Brady LLP; Yakov Sidorin

(57) ABSTRACT

In one embodiment, an optical spectroscopy probe includes an optical fiber having a distal tip and a microfluidic filtering chamber attached to the distal tip of the optical fiber, the chamber comprising a microfluidic membrane adapted to enable liquid to enter the chamber but prevent particles from entering the chamber.

19 Claims, 9 Drawing Sheets

(51) Int. Cl.
   G02B 6/36   (2006.01)
   G01N 33/49  (2006.01)
   A61B 5/00   (2006.01)
   G01N 21/39  (2006.01)
   B01D 63/00  (2006.01)

(52) U.S. Cl.
   CPC ...... A61B 5/4244 (2013.01); B01L 3/502707 (2013.01); B01L 3/502715 (2013.01); G01N 21/39 (2013.01); G02B 6/3628 (2013.01); B01D 63/005 (2013.01); B01L 2300/0654 (2013.01); B01L 2300/0681 (2013.01); B01L 2300/168 (2013.01); G01N 2201/06113 (2013.01); G01N 2201/0846 (2013.01)

(56) References Cited

U.S. PATENT DOCUMENTS

| | | | | |
|---|---|---|---|---|
| 5,059,790 | A * | 10/1991 | Klainer | G01N 21/7703 250/227.21 |
| 5,127,406 | A | 7/1992 | Yamaguchi | |
| 5,246,862 | A * | 9/1993 | Grey | G01N 33/24 422/66 |
| 5,344,418 | A | 9/1994 | Ghaffari | |
| 5,701,181 | A | 12/1997 | Boiarski | |
| 6,157,442 | A | 12/2000 | Raskas | |
| 6,256,522 | B1 | 7/2001 | Schultz | |
| 6,411,907 | B1 * | 6/2002 | Lu | A61B 5/0059 702/28 |
| 6,488,891 | B2 | 12/2002 | Mason | |
| 7,790,464 | B2 | 9/2010 | Tarasev | |
| 7,792,561 | B2 | 9/2010 | Alarcon | |
| 7,821,620 | B2 | 10/2010 | Dogariu | |
| 2002/0026108 | A1 | 2/2002 | Colvin | |
| 2003/0003587 | A1 | 1/2003 | Murray | |
| 2004/0228568 | A1 * | 11/2004 | Letant | G01N 21/774 385/12 |
| 2005/0014129 | A1 * | 1/2005 | Cliffel | G01N 33/5041 205/777.5 |
| 2007/0038124 | A1 * | 2/2007 | Fulghum, Jr. | A61B 5/0071 600/476 |
| 2011/0097755 | A1 * | 4/2011 | Nomura | G01N 33/528 435/14 |
| 2015/0174573 | A1 * | 6/2015 | Esch | G03F 7/2022 430/320 |

OTHER PUBLICATIONS

Gulari, et al., "A compact, optofluidic system for measuring red blood cell concentration", The 17th International Conference on Transducers and Eurosensors XXVII, 2013.
M. E. H. Ong, Y. H. Chan, and C. S. Lim, "Reducing blood sample hemolysis at a tertiary hospital emergency department," The American journal of medicine, vol. 122, p. 1054. e1-1054. e6, 2009.
M. Stauss, B. Sherman, L. Pugh, D. Parone, K. Looby-Rodriguez, A. Bell, and C.-R. Reed, "Hemolysis of Coagulation Specimens: A Comparative Study of Intravenous Draw Methods," Journal of Emergency Nursing, vol. 38, pp. 15-21, 2012.
G. Lippi, M. Plebani, A.-M. Simundic, C. Mattiuzzi, M. M. Müller, O. Sonntag, L. Sciacovelli, S. Secchiero, and L. Zardo, "Special issue: Quality in laboratory diagnostics: from theory to practice," Biochemia Medica, vol. 20, pp. 126-130, 2010.
R. N. Makroo, V. Raina, A. Bhatia, R. Gupta, A. Majid, U. K. Thakur, and N. L. Rosamma, "Evaluation of Red Cell Hemolysis in Packed Red Cells During Processing and Storage," Apollo Medicine, vol. 7, pp. 35-38, 2010.
McGrath, J. K, Rankin, P., & Schendel, M. (2012). Let the Data speak: Decreasing Hemolysis Rate Through Education, Practice, and Disclouse. Journal of Emergency Nursing (3), 239 doi:10.1016/j.jen.2011 01.015.

N. J. Heyer, J. H. Derzon, L. Winges, C. Shaw, D. Mass, S. R. Snyder, P. Epner, J. H. Nichols, J. A. Gayken, D. Ernst, and E. B. Liebow, "Effectiveness of practices to reduce blood sample hemolysis in EDs: A laboratory medicine best practices systematic review and meta-analysis," Clinical Biochemistry, vol. 45, pp. 1012-1032, 2012.
B.A. Jones, R.R. Calam & P.J. Howanitz, Arch Pathology laboratory Medicine, 1997,121, 19-26.
World Health Organization (WHO). World Health report 205: Make Every Mother and Child Count. Geneva: WHO; 2005, p. 63.
E. Ciantar and J. J. Walker, "Pre-eclampsia, severe pre-eclampsia and hemolysis, elevated liver enzymes and low platelets syndrome: what is new?," Women's Health, vol. 7, pp. 555-569, 2011.
E. V. Kuklina, C. Ayala, and W. M. Callaghan, "Hypertensive disorders and severe obstetric morbidity in the United States," Obstetrics & Gynecology, vol. 113, pp. 1299-1306, 2009.
B. E. Jones, "Optical fibre sensors and systems for industry," Journal of Physics E: Scientific Instruments, vol. 18, p. 770, 1985.
VanDelinder, V., & Groisman, A. (2006). Separation of Plasma from Whole Human Blood in a Continuous Cross-Flow in a Molded Microfluidic Device Analytical Chemistry, 78(11), 3765-3771. doi: 10.1021/ac060042r.
A. Liu, L. Liao, D. Rubin, H. Nguyen, B. Ciftcioglu, Y. Chetrit, N. Izhaky, and M. Paniccia, "High-speed optical modulation based on carrier depletion in a silicon waveguide," Opt. Express, vol. 15, pp. 660-668, 2007,J. Hecht and L. Long, Understanding fiber optics vol. 3: Prentice Hall Upper Saddle River, NJ, 2002.
J. S. Mckenzie and C. Clark, "High sensitivity micromachined optical-to-fluid pressure converter for use in an optical actuation scheme," Journal of Micromechanics and Microengineering, vol. 2, p. 245, 1992.
V. Fairbanks, S. Ziesmer, and P. O'Brien, "Methods for measuring plasma hemoglobin in micromolar concentration compared," Clinical chemistry, vol. 38, pp. 132-140, 1992.
Crowley, T. A., & Pizziconi, V. (2005). Isolation of plasma from whole blood using planar microfilters for lab-on-a-chip applications. Lab on a Chip, 5(9), 922-929. doi: 10.1039/B502930A.
S. Gonchukov, Y. B. Lazarev, and A. Podkolzin, "Laser Refractometry of Biological Media," Laser Physics-Lawrence-, vol. 9, pp. 344-347, 1999.
Y. L. Jin, J. Y. Chen, L. Xu, and P. N. Wang, "Refractive index measurement for biomaterial samples by total internal reflection," Physics in Medicine and Biology, vol. 51, p. N371, 2006.
M. Zolkapli, A. Zoolfakar, A. Manut, S. Taniselass, and P. Poopalan, "Design and fabrication of microfluidic transistor on silicon subsliale," in Micro and Nanoelectronics (RSM), 2011 IEEE Regional Symposium on, 2011, pp. 96-99.
S. J. Li, C. Shen, and P. M. Sarro, "A Buried Vertical Filter for Micro and Nanoparticle Filtration," Procedia Engineering, vol. 25, pp. 1193-1196, 2011.
H. K. Lin, S. Zheng, A. J. Williams, M. Balic, S. Groshen, H. I. Scher, M. Fleisher, W. Stadler, R. H. Datar, Y. C. Tai, and R. J. Cote, "Portable filter-based microdevice for detection and characterization of circulating tumor cells," Clin Cancer Res, vol. 16, pp. 5011-5018, Oct. 15, 2010.
Y. Ishii, R. Kaminose, and M. Fukuda, "Optical waveguiding in an electrospun polymer nanofiber," Journal of Physics: Conference Series, vol. 433, p. 012006, 2013.
B. Kim, S. J. Cho, T. An, H. Ryu, H. Lim, and G. Lim, "Optical switching patterns using electrospun nanofiber array," physica status solidi (RRL)—Rapid Research Letters, vol. 6, pp. 409-441, 2012.
C. Van Rijn, M. van der Wekken, W. Nijdam, and M. Elwenspoek, "Deflection and maximum load of microfiltration membrane sieves made with silicon micromachining," Microelectromechanical Systems, Journal of, vol. 6, pp. 48-54, 1997.
J. Wang, E. S. Wong, J. C. Whitley, J. Li, J. M. Stringer, K. R. Short, M. B. Renfree, K. Belov, and B. G. Cocks, "Ancient antimicrobial peptides kill antibiotic-resistant pathogens: Australian mammals provide new options," PLoS One, vol. 6, p. e24030, 2011.
K. Reddy, R. Yedery, and C. Aranha, "Antimicrobial peptides: premises and promises," International journal of antimicrobial agents, vol. 24, pp. 536-547, 2004.

(56) References Cited

OTHER PUBLICATIONS

A. Izadpanah and R. L. Gallo, "Antimicrobial peptides," Journal of the American Academy of Dermatology, vol. 52, pp. 381-390, 2005.

R. Bals and J. Wilson, "Cathelicidins—a family of multifunctional antimicrobial peptides," Cellular and Molecular Life Sciences CMLS, vol. 60, pp. 711-720, 2003.

H. Zhu and M. Snyder, "Protein chip technology," Current Opinion in Chemical Biology, vol. 7, pp. 55-63, 2003.

L. Baldini, A. J. Wilson, J. Hong, and A. D. Hamilton, "Pattern-based detection of different proteins using an array of fluorescent protein surface receptors," Journal of the American Chemical Society, vol. 126, pp. 5656-5657, 2004.

M. S. Bronze and R. A. Greenfield, "Preventive and therapeutic approaches to viral agents of bioterrorism," Drug discovery today, vol. 8, pp. 740-745, 2003.

N. A. Rakow and K. S. Suslick, "A colorimetric sensor array for odour visualization," Nature, vol. 406, pp. 710-713, 2000.

B. J. White, "Porphyrins as colorimetric indicators for detection and identification of chemical and biological agents," Oklahoma State University, 2004.

L. Tomasinsig and M. Zanetti, "The cathelicidins-structure, function and evolution," Current Protein and Peptide Science, vol. 6, p. 23 34, 2005.

H. J. Harmon, "Specific visible spectral changes induced by guanine binding to cytosine-derivatized porphyrin," Journal of Porphyrins and Phthalocyanines, vol. 6, pp. 73-77, 2002.

C. Malitesta, I. Losito, and P. G. Zambonin, "Molecularly Imprinted Electrosynthesized Polymers: New Materials for Biomimetic Sensors," Analytical Chemistry, vol. 71, pp. 1366-1370, Jan. 4, 1999 1999.

M. Takahashi, A. Ueno, T. Uda, and H. Mihara, "Design of novel porphyrin-binding peptides based on antibody CDR," Bioorganic & Medicinal Chemistry Letters, vol. 8, pp. 2023-2026, 1998.

R. K. Jain and A. D. Hamilton, "Protein surface recognition by synthetic receptors based on a tetraphenylporphyrin scaffold," Organic letters, vol. 2, pp. 1721-1723, 2000.

J. R. Deschamps, P. T. Charles, A. P. Malanoski, B. J. Johnson, B. J. Melde, N. E. Anderson, and M. Nasir, "Porphyrin-Embedded Silicate Materials for Detection of Hydrocarbon Solvents," ed: Naval Research Lab Washington Dc Center for Biomolecular Science and Engineering, 2011.

B. Johnson-White, M. Zeinali, K. M. Shaffer, C. H. Patterson Jr, P. T. Charles, and M. A. Markowitz, "Detection of organics using porphyrin embedded nanoporous organosilicas," Biosensors and Bioelectronics, vol. 22, pp. 1154-1162, 2007.

J. A. Legako, B. J. White, and H. J. Harmon, "Detection of cyanide using immobilized porphyrin and myoglobin surfaces," Sensors and Actuators B: Chemical, vol. 91, pp. 128-132, 2003.

* cited by examiner

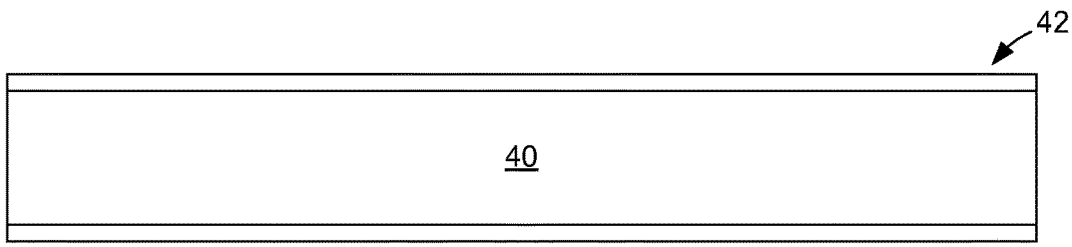
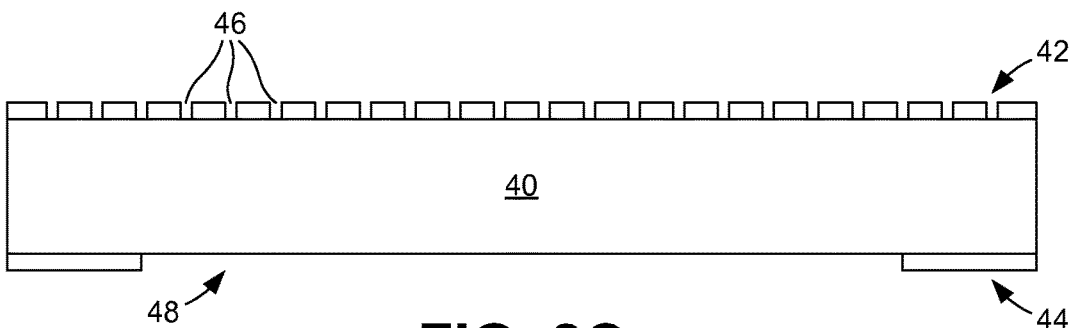
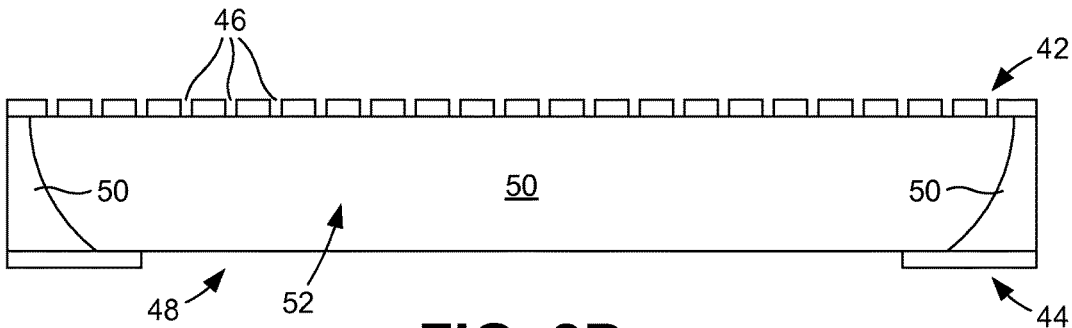
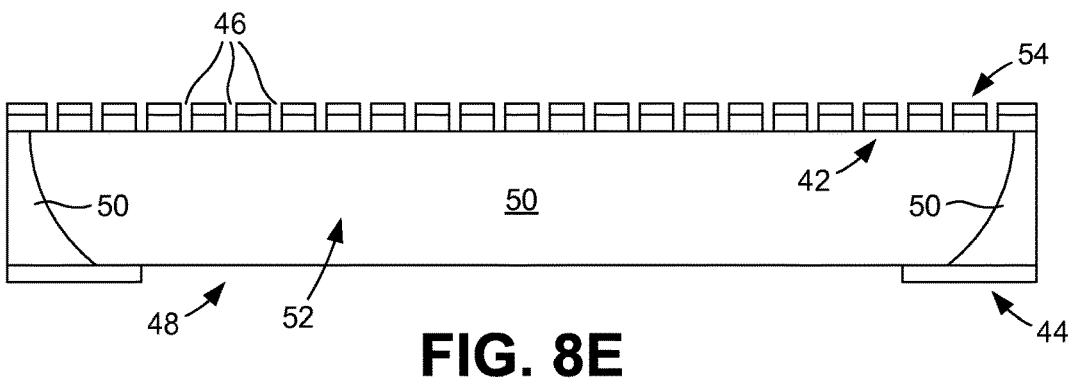

ated liquid using a microfluidic membrane.
SYSTEMS AND METHODS FOR ANALYZING LIQUIDS

CROSS-REFERENCE TO RELATED APPLICATION

This application is the 35 U.S.C. § 371 national stage of, and claims priority to and the benefit of, PCT application PCT/US2015/031366, filed May 18, 2015, which claims priority to and the benefit of U.S. Application No. 62/000,130, filed on May 19, 2014, the entire contents of each which are hereby incorporated herein by reference.

BACKGROUND

There are various situations in which it is desirable to analyze a liquid to determine the makeup of its contents. One example is hemolysis detection. Hemolysis is the disruption of red blood cells and release of hemoglobin and other intercellular components into the blood plasma. Hundreds of millions of blood tests are performed annually in the United States and a significant number of these tests are compromised because of in vitro hemolysis. Unfortunately, there is currently no reliable way to detect hemolysis without plasma separation. Therefore, significant delays are introduced that negatively affect treatment and diagnosis of the patients. If early signs of in vivo hemolysis could be detected, it would significantly improve the outcome for many patients, including pregnant women affected by HELLP syndrome, which is characterized by hemolysis, elevated liver enzymes, and low platelet count.

Another situation in which it may be desirable to analyze a liquid is drug identification. Drug administration errors account for approximately 32% of preventable medical errors that result in morbidity or mortality. While there are several specialized assay-based techniques have been used to monitor medication errors in specific therapeutic treatments, these techniques have several limitations that prevent them from being used for point-of-care sensing. The techniques are time consuming and often require large volumes of analyte to achieve the needed sensitivity. Furthermore, drug assays use complicated electrochemical measurements, suffer from background interference in complex solutions, and have poor thermal stability.

In view of the above discussion, it can be appreciated that there is a critical need for a system and method that enables real-time, point-of-care analysis of liquids.

BRIEF DESCRIPTION OF THE DRAWINGS

The present disclosure may be better understood with reference to the following figures. Matching reference numerals designate corresponding parts throughout the figures, which are not necessarily drawn to scale.

FIGS. 8A-8E illustrate sequential steps in an embodiment of a microfluidic filtering chamber fabrication process.

DETAILED DESCRIPTION

As described above, there is a critical need for a system and method that enables real-time, point-of-care analysis of liquids. Disclosed herein are examples of such systems and methods. In some embodiments, a system comprises an optical spectroscopy probe that includes a microfluidic filtering chamber that is used in conjunction with an optical fiber. The chamber of the probe can be immersed in a liquid and used to filter out components within the liquid that could otherwise skew the analysis results. The liquid can, for example, be a biological fluid, such as blood, or a fluid that is to be administered to a patient, such as intravenous fluid. Regardless, the chamber separates free-floating particles in the fluid from the remainder of the fluid to enable absorption spectroscopy to be performed on the fluid.

One goal for the disclosed systems and methods is to replace traditional hemolysis testing of blood samples, which requires larges volume of blood to be collected, centrifugation, and bulk instrumentation, with a single setup that can work nearly instantaneously. A miniature, near-patient sensor for the detection of hemolysis will enhance patient diagnosis, treatments, costs, satisfaction, and experience. Another goal for the disclosed systems and methods is to overcome the limitations of drug identification testing by providing a new platform that can be used to detect the concentrations of drugs within a liquid by absorption spectroscopy, free of noise from particles and cells, without prior sample pre-processing.

Figure 1:
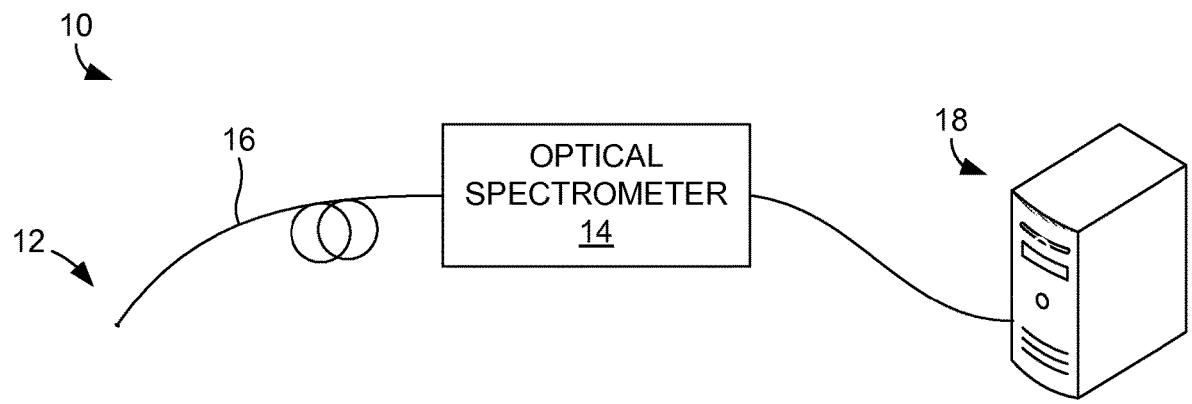
FIG. 1 is a schematic diagram of an embodiment of a system for analyzing liquids.

These goals can be achieved through use of an optical spectroscopy system that comprises an optical spectroscopy probe that can be directly inserted into a liquid such as blood (in vivo or in vitro) or a solution that is to be administered to a patient. FIG. 1 illustrates an example embodiment of such a system. As shown in the figure, the system 10 generally comprises an optical spectroscopy probe 12 that is coupled to an optical spectrometer 14 that can detect the intensity of absorbed light as a function of wavelength or frequency. The probe 12 includes an optical fiber 16 and a microfluidic filtering chamber (not visible in FIG. 1) that is provided at a distal end of the fiber. The optical spectrometer 14 is connected to a computing device 18 that executes software that can perform analysis on the light detected by the spectrometer and output conclusions based upon the analysis.

Figure 2:
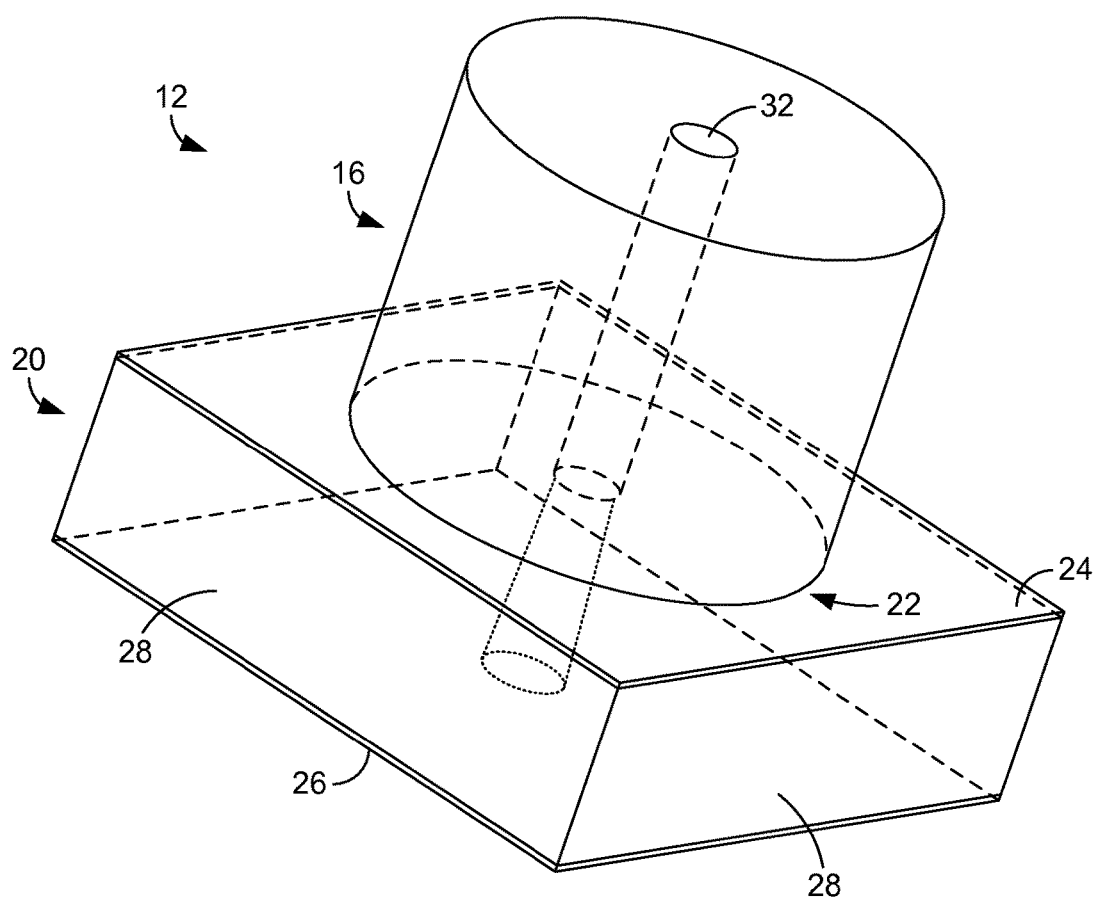
FIG. 2 is a partial perspective view of an embodiment of an optical spectroscopy probe that can be used in the system of FIG. 1.
Figure 4:
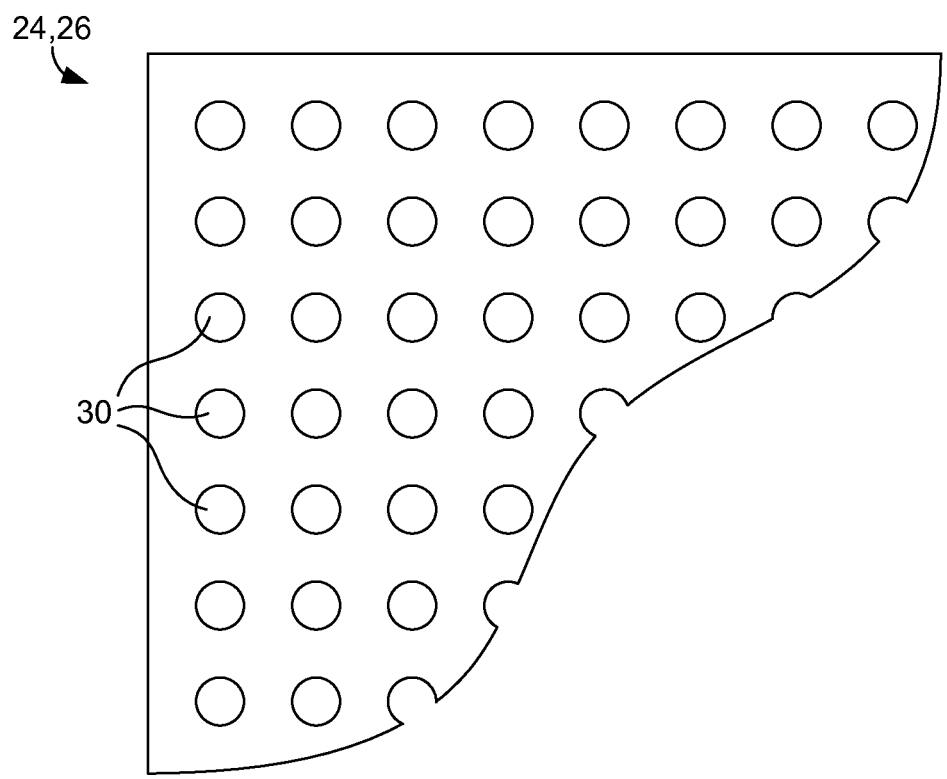
FIG. 4 is a partial plan view of a wall of the microfluidic filtering chamber of FIG. 3.

FIG. 2 illustrates an example configuration for the optical spectroscopy probe 12. As shown in this figure, the probe 12 comprises the optical fiber 16 identified in FIG. 1 and a microfluidic filtering chamber 20 that is attached to a cleaved distal tip 22 of the fiber. As shown in this figure, the microfluidic filtering chamber 20 is configured as a generally rectangular box that is defined by a proximal (or top) wall 24, a distal (or bottom) wall 26, and multiple side walls 28. The proximal wall 24 and the distal wall 26 can be made of silicon nitride ($Si_3N_4$) and can be approximately 0.3 to 3 μm thick and have length and width dimensions of approximately 100 to 3,000 μm. The distal wall 26, and optionally the proximal wall 24, is perforated so as to comprise a plurality of pores that form a microfluidic filter or membrane through which fluid can flow, but particles larger than the pores cannot. FIG. 4 shows a partial detail view of one of the walls 24, 26. As indicated in this figure, the pores 30 can be generally circular and equidistantly spaced from each other across the plane of the wall 24, 26. In some embodiments, the pores 30 are approximately 1 to 10 μm in diameter or width.

Figure 3:
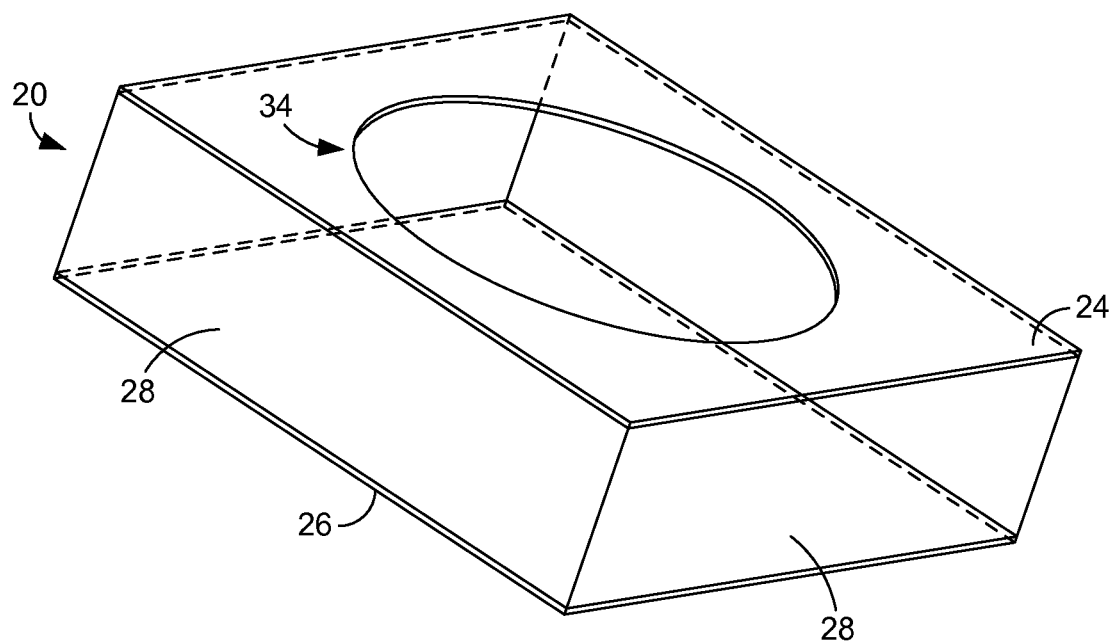
FIG. 3 is a perspective view of a microfluidic filtering chamber of the optical spectroscopy probe of FIG. 2.

Referring back to FIG. 2, the side walls 28 can be made of silicon and can be approximately 100 to 1,000 μm tall and approximately 10 to 500 μm thick. The optical fiber 16 can be approximately 100 to 400 μm in diameter and can have a core 32 that is approximately 8 to 50 μm in diameter. As shown in FIG. 3, which depicts the microfluidic filtering chamber 20 separate from the optical fiber 16, the proximal wall 24 of the chamber 20 can have an opening 34 that is sized and configured to receive the distal tip 22 of the fiber. This opening 34 can also have a diameter of approximately 100 to 400 μm.

The distal wall 26 can be reflective to enable spectroscopic measurement of the fluid under evaluation. In some embodiments, the outer surface 36 of the distal wall 26 is coated with a reflective material, such as a reflective metal (see FIG. 5).

Figure 5:
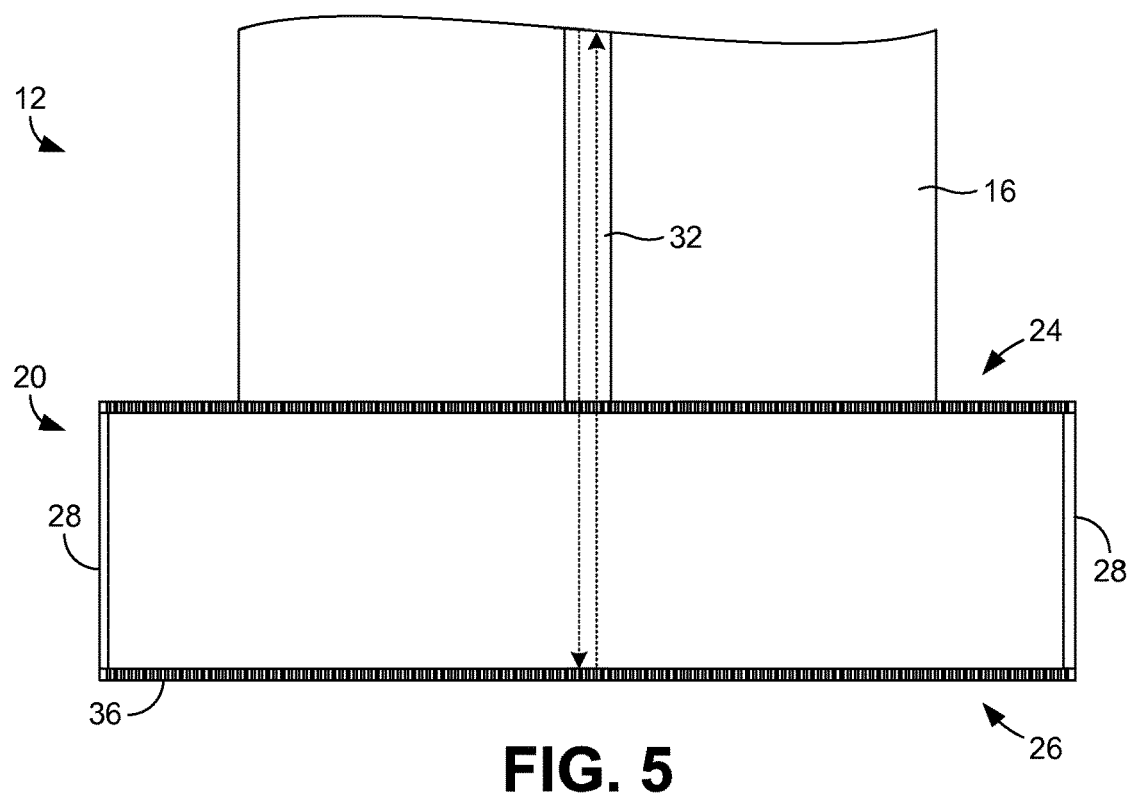
FIG. 5 is a schematic side view of the optical spectroscopy probe of FIG. 2, illustrating reflection of light emitted from an optical fiber of the probe.

During use, the microfluidic filtering chamber 12 can be used to locally separate particles from fluid, which collects inside the chamber. For example, if the fluid is whole blood, the chamber 12 can separate red blood cells from the blood plasma. Because the distal wall 26 is reflective, light exiting the core 32 of the optical fiber 16 will propagate through the filtered liquid, reflect off of the distal wall, and couple back into the core, as depicted in FIG. 5. Hemolysis can be detected by measuring increased hemoglobin-related absorption in the locally filtered plasma. In some embodiments, the light has a wavelength that exhibits high hemoglobin absorption, such as approximately 532 nm. Alternatively, if the fluid is one that is to be administered to a patient, the absorption of the light by the fluid can provide an indication of a drug present in the fluid and its concentration.

Figure 6A:
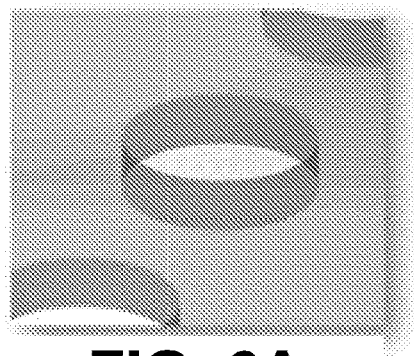
FIGS. 6A-6D are renderings of microfluidic membranes having various pore sizes.
Figure 6B:
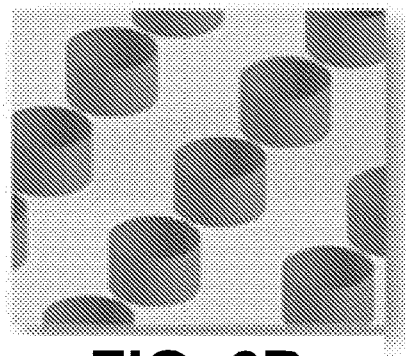
Figure 6C:
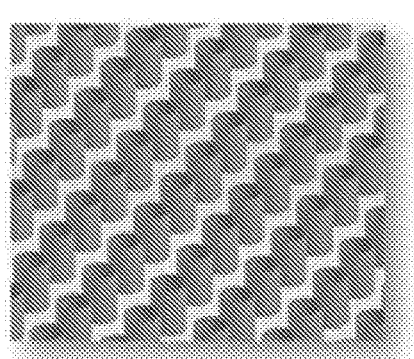
Figure 6D:
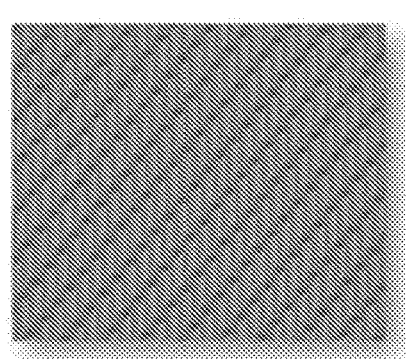
Figure 7:
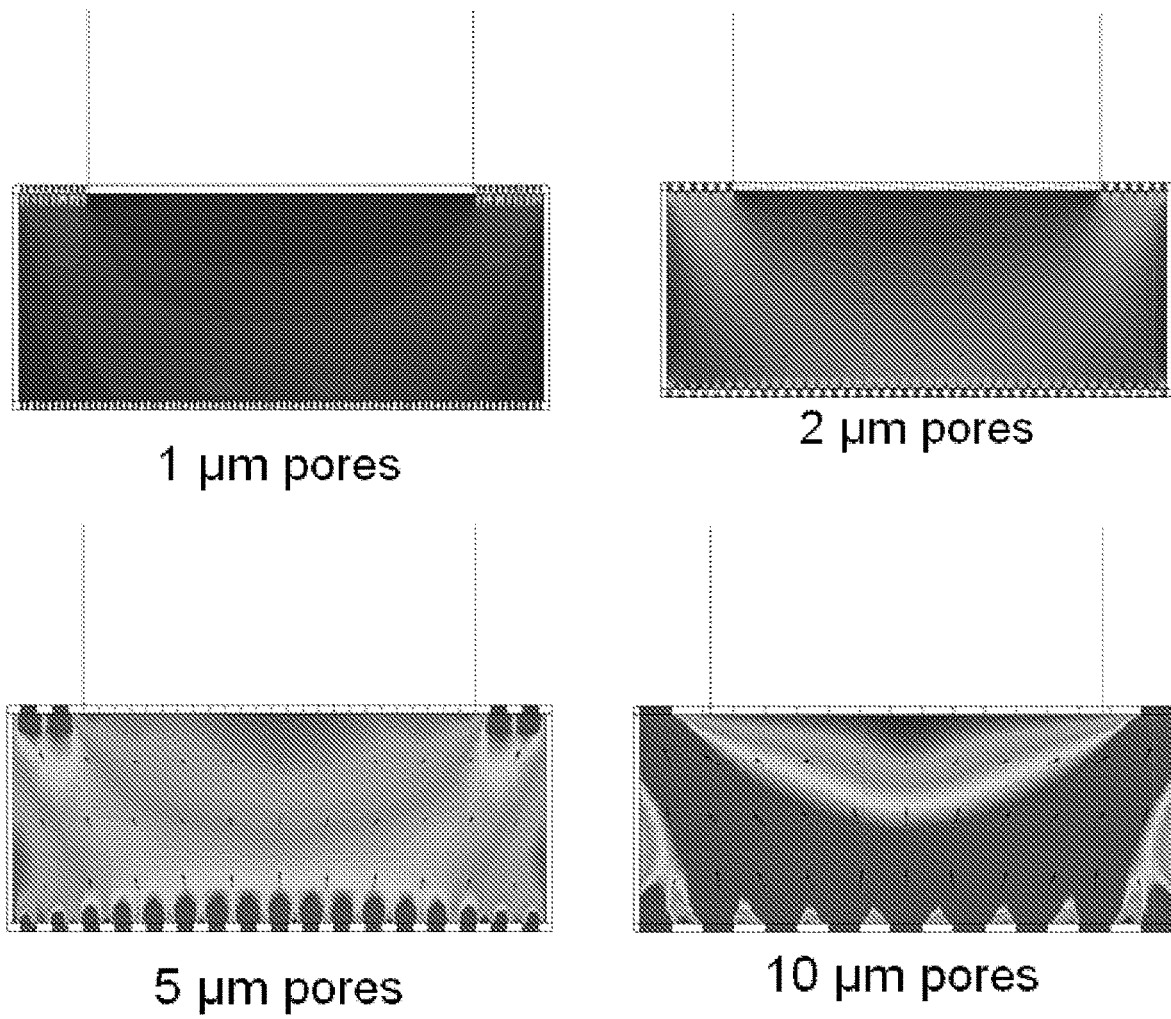
FIG. 7 includes graphs of the velocity and vector fields inside microfluidic chambers having various pore sizes.

SolidWorks™ was used to evaluate different perforation configurations. FIGS. 6A 6D are SolidWorks™ renderings of microfluidic membranes having pore sizes of 1, 2, 5, and 10 μm. The optimal pore size that will allow sufficient fluid flow inside the device was determined using only minimum external pressure as the driving force. The goal was to determine the smallest optimal pore size that would provide substantial fluid through the membrane while impeding access of the relatively large particles within the chamber in which the membrane could be provided. The fluid simulation was iterated until the bulk average velocity reached steady state. The study showed that, when the membranes have a pore size less than 1 μm, the flow velocity through the membrane is negligible without driving the liquid through the membrane with elevated pressure. Reasonable flow can be achieved starting from 2 μm pores with the speed of flow significantly increasing for 5 and 10 μm (see FIG. 7). In view of this, for applications in which no driving force is provided, the optimal pore size may be around 2 μm. For smaller pore sizes, additional pressure may need to be applied. Of course, the optimal pore size may also be dependent upon the viscosity of the fluid.

After detailed design optimization was performed, prototype microfluidic filtering chambers were fabricated using standard micro-fabrication processes. FIGS. 8A-8E schematically illustrate steps of one such fabrication process. Beginning with FIG. 8A, a double-sided polished silicon wafer from Nova Electronic Materials (Texas) was used as the membrane substrate 40. Referring next to FIG. 8B, a 1 μm thick layer 42, 44 of silicon nitride was grown on both sides of the substrate 40 using low stress, low pressure chemical vapor deposition (LPCVD). The coated substrate 40 was cleaned with acetone and isopropyl alcohol (IPA) and then dried with nitrogen. Additionally, the substrate 40 was baked on hotplate at 115° C. for 5 minutes to dry it. The substrate 40 was cooled for a few minutes and then spin-coated with photoresist. Next, the $Si_3N_4$ layers were patterned using ultraviolet (UV) photolithography and reactive ion etching to form pores 46 on the layer 42 (i.e., the distal wall) and an optical fiber opening 48 on the opposite layer 44 (i.e., the proximal wall), as shown in FIG. 8C. The pores 46 were 10 μm in diameter and were patterned in a square array with the distance of 15 μm from center to center. This configuration enables filtration of particles larger than 10 μm in diameter.

After patterning the silicon nitride layers 42, 44, the exposed silicon was etched away in a solution of potassium hydroxide (KOH, 85° C.) for 7 hours, to create side walls 50 and a hollow inner chamber 52 between the two nitride layers 42, 44 and the side walls, as shown in FIG. 8D. Finally, as shown in FIG. 8E, a 200 nm layer 54 of gold was deposited on top of the silicon nitride layer 42 using a Denton Thermal Evaporator.

Figure 9:
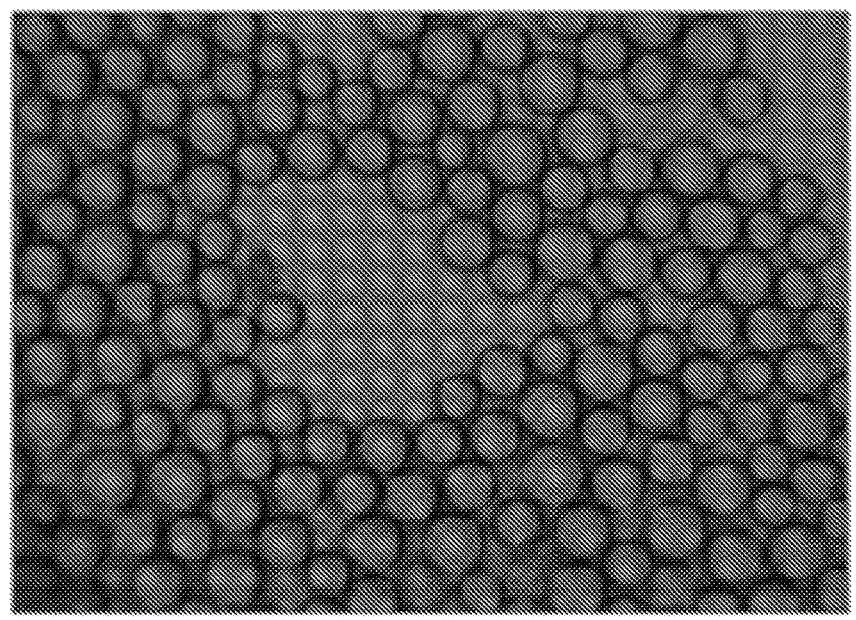
FIG. 9 is an image of a fabricated microfluidic membrane filtering particles that were larger that the pore size of the membrane.
Figure 10:
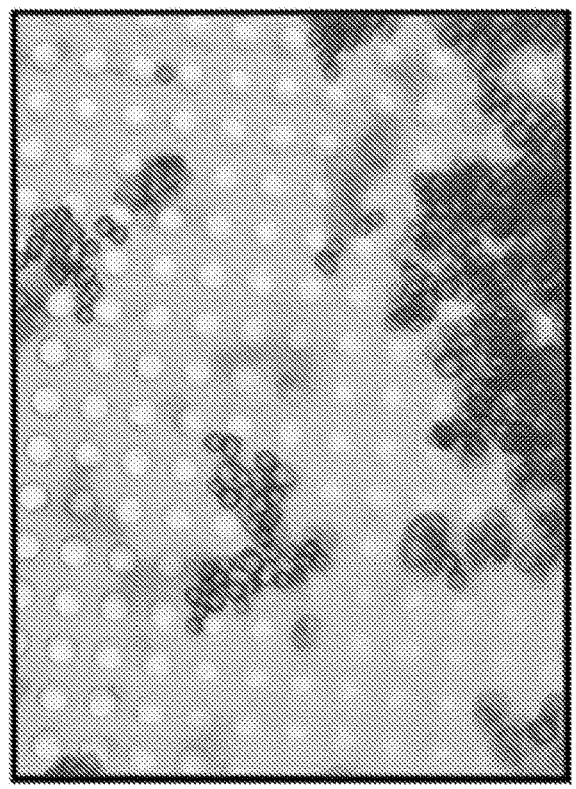
FIG. 10 is an image of small particles having passed through a fabricated microfluidic membrane having pores larger than the particles.

The filtering properties of fabricated membranes were tested using micro-particle filtration. Fluid was pumped through the membranes using a peristaltic pump with a minimum pressure of 2.14 uL/s working at this lowest setting. FIG. 9 shows particles larger than the pore size being stopped by a membrane, while FIG. 10 shows particles smaller than the pore size freely propagating through the pores (particles can be seen on both sides of the transparent membrane in FIG. 10).

After continuous testing using an initial setup with direct fluid drop on the membrane, the delay in filtering was observed due to the accumulation of large number of particles on surface of the membrane. Next, a two-head polydimethylsiloxane (PDMS) microfluidic setup was designed. It was made with a replaceable watertight seal for experiments with different flow parameters while little external pressure was provided using the peristaltic pump. Replaceable capillary tubes were used instead of molding columns for flow on the PDMS and glass slides were used to hold the setup in place.

Figure 11:
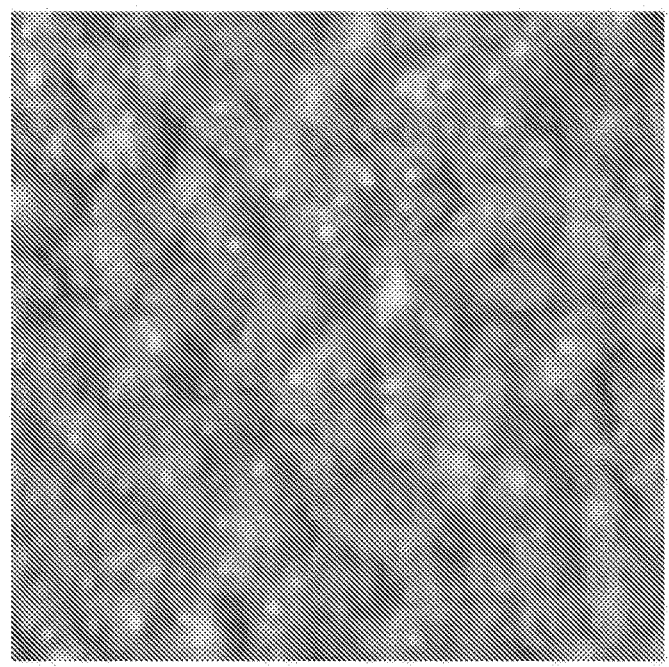
FIG. 11 is an image of cells being blocked by a fabricated microfluidic membrane having pores smaller than the cells.

Next, breast cancer cells in a cell medium were used to demonstrate cell filtering and capture. Using a confocal microscope, images of human breast cancer cell line were captured as droplets of cells in the medium were introduced to the microfluidic membrane. The Hs578t epithelial breast cancer cells, as shown in FIG. 11, are on the larger scale than normal cells and had an average size of 11 µm. The cells clustered on top of the membrane.

In further testing, fabricated membranes were positioned underneath an upright optical microscope for observation, where the membrane surfaces were oriented perpendicular to the microscope objective. The membranes were slightly elevated, allowing for space to exist beneath them. In order to observe filtration with these membranes, a droplet of deionized water containing naturally occurring contaminants (dust) was placed on top of the membrane surface. By relying on gravitational forces alone, the droplet of water was allowed to pass through the membrane, while contaminants were effectively filtered out. These effects were recorded using a microscope camera. After the filtration experiment was completed, the membranes were easily cleaned by rinsing with acetone.

After testing the filtering properties of the membranes, fabricated microfluidic filtering chambers comprising the membranes were attached to optical fiber tips. For this, an 8 µm optical fiber was cleaved and inserted into an adjustable fiber holder to provide mechanical support to the otherwise flexible fiber. Following this, the fiber holder was inserted into a high precision XYZ-stage and the tip was positioned approximately 105 µm from a reflective metal membrane by adjusting the dial of the optical stage. Finally, the entire device was fixed in place by epoxying the metal surrounding the membranes to a small PDMS tube. This tube was created to fit tightly to the optical fiber holder.

In order to optimize coupling, the optical fiber was set perpendicular to the membrane. Angular alignment of the system was performed by adjusting the XYZ-stage and observing the reflected power in air. An approximation of fiber angle was made qualitatively through visual observation. However, for added precision, reflected power was recorded while the fiber angle was finely tuned. The fiber angle was set once the reflected power reach a maximum value. Following angular alignment, the fiber needed to be placed at a set spacing from the membrane surface. The XYZ-stage allows for vertical adjustment of the fiber. However, micron-level precision was needed to effectively determine the spacing, and thus Fabry-Perot resonance was used for high precision measurements. The resonance was formed between the gold-coated membrane and the cleaved fiber interface. The spectrum was recorded in air (refractive index: 1.0) and conducted using infrared light between 1,400 and 1,500 nm. Using the collected infrared (IR) spectrum, the distance could be calculated using the following expression:

$$d = \frac{\lambda_i^2}{2n(\lambda_{i+1} - \lambda_i)} \quad \text{(Equation 1)}$$

where $\lambda_i$ and $\lambda_{i+1}$ are consecutive resonance wavelengths (nm) and n is the refractive index. By recording resonance patterns for different vertical settings of the XYZ-stage, a correlation between stage setting and the actual distance, determined by Equation (1), was obtained. Once the appropriate vertical setting was found, the fiber was fixed in position and the distance was verified again using Fabry-Perot resonance. The Fabry-Perot resonance was recorded for the vertical setting once the fiber was set 105 µm from the membrane.

In order to demonstrate that the microfluidic filtering chamber is capable of identifying drugs and their concentrations, absorption spectroscopy was conducted for cobalamin (vitamin $B_{12}$). Cobalamin is an essential water-soluble vitamin, of which a deficiency can lead to abnormal neurologic and psychiatric symptoms. There are a variety of doses that are used for injections, from 0.2 µg/kg for neonates and infants to 1,000 µg/kg total for adults with severe vitamin deficiency.

Figure 12:
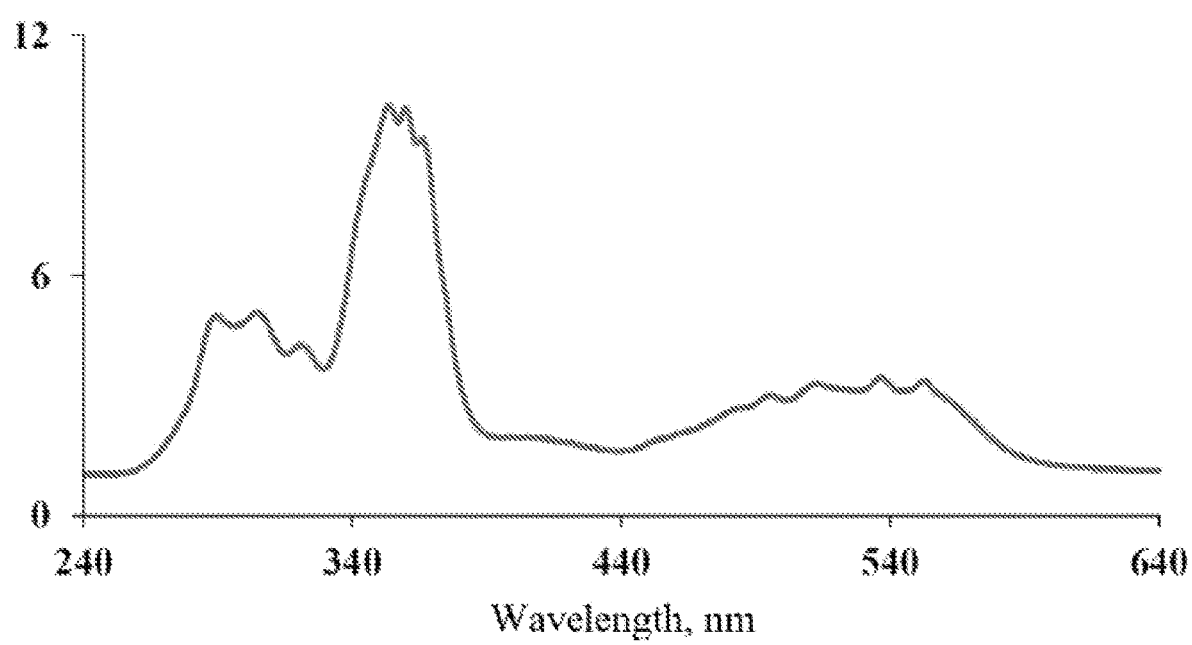
FIG. 12 is a graph that shows the theoretical absorption spectrum for cobalamin.
Figure 13:
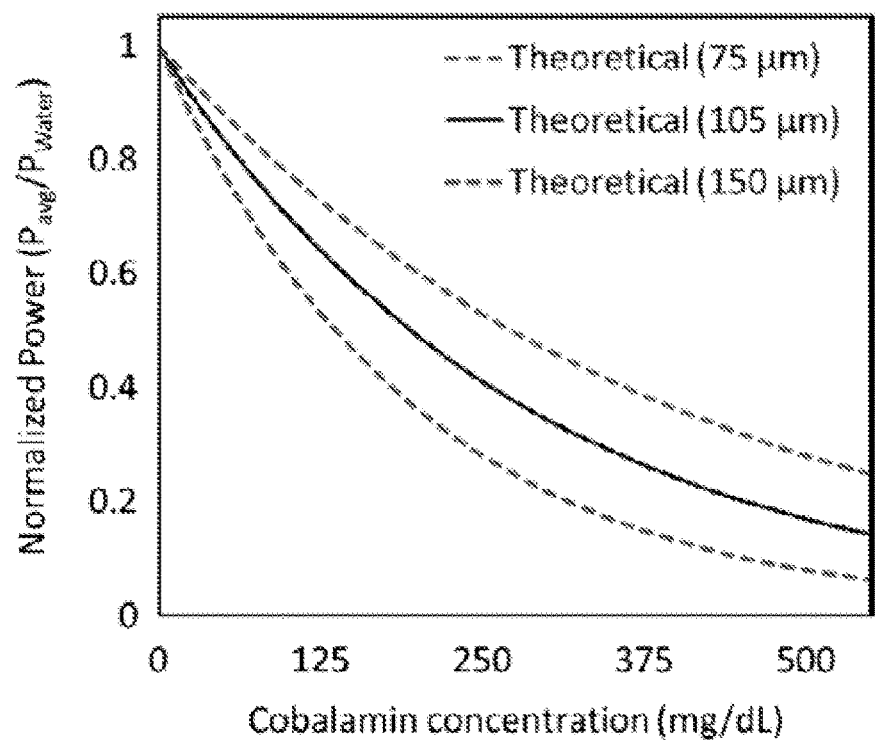
FIG. 13 is a graph that shows cobalamin measurements when an optical fiber was spaced from a reflective microfluidic membrane at distances of 75, 105, and 150 µm.

The absorption spectrum of cobalamin dissolved in water with a concentration of 60 mg/dL is shown in FIG. 12. When drug is known, its concentration can be measured at one specific wavelength, since it is much faster than measurements of the whole spectrum. The goal was to construct a sensor that would be able to conduct measurements for the broad range of concentrations from 0.1 mg/dL to 500 mg/dL. Theoretical modeling of this sensors transfer function was conducted using Beer-Lambert law:

$$\frac{P}{P_o} = \exp(-2\alpha dC) \quad \text{(Equation 2)}$$

where P is the power of transmitted light (W) for the fluid under study, $P_o$ is the transmitted power (W) for a pure sample, $\alpha$ is the molar absorptivity with units of L/mol cm, 2d is the total optical path where d was the spacing between the fiber and reflective surface (cm), and C is the concentration of the cobalamin expressed in mol/L. FIG. 13 shows the theoretical transfer functions plotted for the needed range of concentrations with 75, 105, and 150 µm spacing between the fiber and the membrane. While the 150 µm gap is better for the measurements of lower concentrations and the 75 µm works better for higher concentrations, the 105 µm gap is suitable for both ranges and thus was chosen for the experimental testing.

During the experiments, the concentration of cobalamin was varied from approximately 0.1 to 515 mg/dL while the reflected power was recorded for each concentration. All measurements were conducted over 5 minute timeframes, during which the power was averaged. A high stability green laser (532 nm) was used at a fixed power at 30 mW. After a cobalamin measurement was made, the sample was removed, and the sensor was thoroughly rinsed with water. This cleaning was conducted to prevent build-up of cobalamin on surfaces. After cleaning, the setup was allowed to air dry for approximately 1 minute, ensuring that all water was removed from the system. Samples were tested sequentially with increasing concentration. In order to ensure reproducibility of results, every test was calibrated with respect to the water control measurements.

Figure 14:
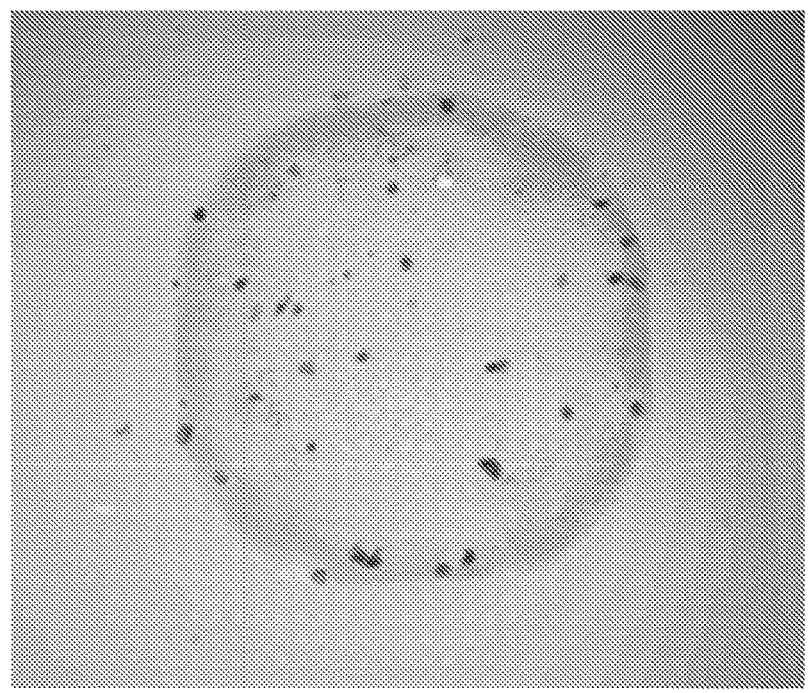
FIG. 14 is an image illustrating microfiltration of a liquid using a microfluidic membrane.

As previously mentioned, the filtering properties of the microfabricated porous membrane were demonstrated with a drop of deionized water. The water passed through the pores in the membrane and forms a drop on the other side, while all particles were filtered by the pores and remained on the membrane surface (see FIG. 14). FIG. 14 demonstrates the outline of the water drop that is not fully seen since it is already under the membrane and the dark spots are particles that are present in all real world samples and were successfully filtered out by the membrane. For cleaning purposes, the membrane was flushed with acetone. It was observed that this also improved its wetting properties. While without applying additional pressure, water takes several minutes to completely pass through the membrane. However, prior prewashing decreases this time to seconds. The membrane was also tested continuously with the lowest setting of a peristaltic pump pumping fluid with the flow rate approximately 2 μL/s, and it could withstand the external pressure still demonstrating successful particle filtration.

Figure 15:
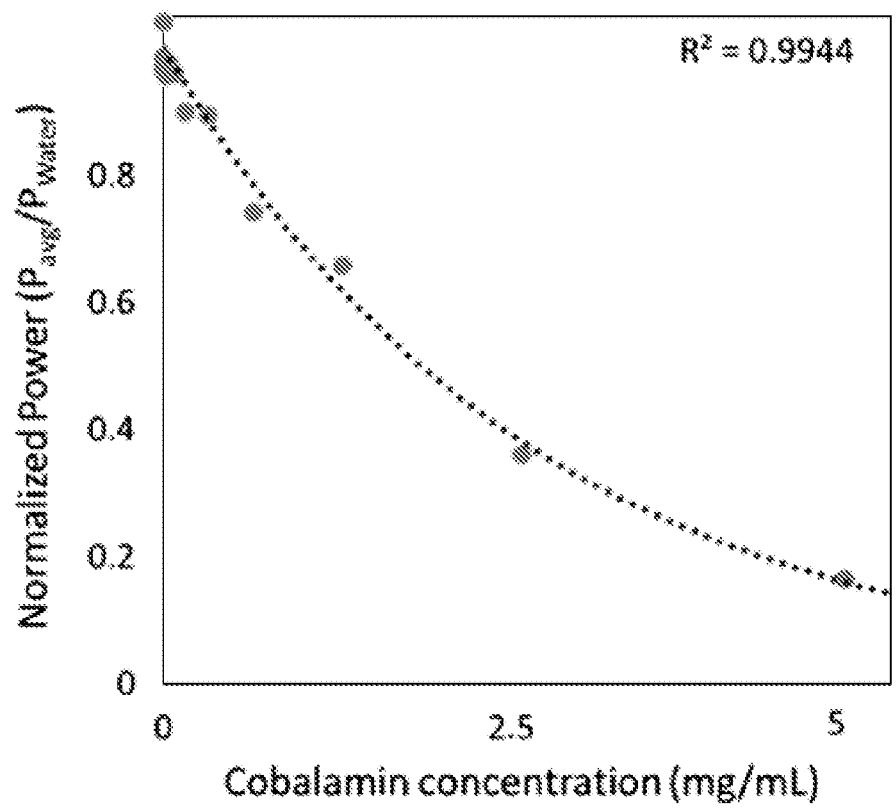
FIG. 15 is a graph that shows the results of optical measurement of cobalamin concentrations.

The aforementioned 0.2 μg/kg to 1,000 μ/kg dosage range translates to a range of concentrations from 1 μg/ml to 1,000 μg/ml. FIG. 15 shows measurements of concentrations between 1 μg/mL to 5 mg/mL to monitor the physiological range and potential overdose. Because cobalamin was the only compound sensed, all the measurements were conducted with a single wavelength, 532 nm, where cobalamin has high absorption and the sensor would have the highest sensitivity. The experimental points are well fitted by the theoretical curve obtained using Beer-Lambert Law ($R^2$=0.994).

Various specific embodiments have been described in the preceding disclosure. It is to be understood that those embodiments are example implementations of the disclosed inventions and that alternative embodiments are possible. All such embodiments are intended to fall within the scope of this disclosure.

The invention claimed is:

1. An optical spectroscopy probe comprising:
   an optical fiber having a distal tip; and
   a microfluidic filtering chamber,
   wherein the microfluidic filtering chamber is defined by sidewalls defined in a silicon substrate and silicon nitride thin-films capping the side walls and forming a top and a bottom of the microfluidic filtering chamber, the side walls and the silicon nitride thin-films enclosing a hollow inner space of the chamber configured to receive a liquid to be analyzed,
   wherein at least one of the silicon nitride thin-films comprises a plurality of pores that allow liquid to enter the hollow inner space but prevent particles larger than the pores from entering the hollow inner space,
   wherein the silicon nitride thin-films include a proximal thin-film that is in contact with the optical fiber and a distal thin-film that is distant from the optical fiber.

2. The probe of claim 1, wherein distal thin-film comprises the plurality of pores.

3. The probe of claim 1, wherein the pores are approximately 1 μm to 10 μm in diameter or width.

4. The probe of claim 1, wherein the distal thin-film is reflective so as to reflect light emitted from the distal tip of the optical fiber back to the optical fiber.

5. The probe of claim 4, wherein an outer surface of the distal thin-film is coated with a reflective metal.

6. The probe of claim 1, wherein the proximal thin-film comprises the plurality of pores.

7. The probe of claim 1, wherein the proximal thin-film comprises an opening adapted to receive the distal tip of the optical fiber.

8. The probe of claim 1, wherein the side walls and the silicon nitride thin-films together form a rectangular box that defines the hollow inner space.

9. The probe of claim 1, wherein the silicon substrate is approximately 100 μm to 1000 μm thick.

10. The probe of claim 9, wherein the silicon nitride thin-films are approximately 0.3 μm to 3 μm thick.

11. The probe of claim 10, wherein the silicon substrate and the silicon nitride thin-films are approximately 100 μm to 3000 μm in length and width.

12. An optical spectroscopy probe comprising:
    an optical fiber having a distal tip; and
    a microfluidic filtering chamber comprising a proximal thin-film layer that is in contact with the distal tip of the fiber and that is made of silicon nitride, a distal thin-film layer made of silicon nitride, and one or more side walls that are made of silicon and that extend between and are limited in extent by the proximal thin-film layer and the distal thin-film layer,
    wherein the proximal thin-film layer, distal thin-film layer, and said one or more side walls define and enclose a hollow inner space of the chamber configured to receive a liquid to be analyzed,
    wherein the proximal thin-film layer has an opening in which the distal tip of the optical fiber is received,
    wherein at least one of the proximal thin-film layer, and the distal thin-film layer, comprises a plurality of pores that allow the liquid to enter the hollow inner space but prevent particles larger than the pores from entering the hollow inner space.

13. The probe of claim 12, wherein the distal thin-film layer is reflective so as to reflect light emitted from the distal tip of the optical fiber back to the optical fiber.

14. The probe of claim 13, wherein an outer surface of the distal thin-film layer is coated with a reflective metal.

15. The probe of claim 12, wherein the pores are approximately 1 μm to 10 μm in diameter or width.

16. The probe of claim 12, wherein the proximal wall and the distal wall are each approximately 0.3 μm to 3 μm thick.

17. The probe of claim 12, wherein the one or more side walls are each approximately 100 μm to 500 μm thick.

18. The probe of claim 2, wherein the distal thin-film includes a layer of gold.

19. The probe of claim 12, wherein the distal thin-film layer includes a layer of gold.

\* \* \* \* \*